(12) United States Patent
Potter et al.

(10) Patent No.: US 6,392,038 B1
(45) Date of Patent: May 21, 2002

(54) PROCESS FOR PREPARING SINGLE ENANTIOMER NARWEDINE

(75) Inventors: Gerard Andrew Potter, Leicester; Peter David Tiffin, Cambridge, both of (GB)

(73) Assignee: Janssen Pharmaceutica, N.V. (BE)

( * ) Notice: Subject to any disclaimer, the term of this patent is extended or adjusted under 35 U.S.C. 154(b) by 0 days.

(21) Appl. No.: 09/402,722

(22) PCT Filed: Apr. 8, 1998

(86) PCT No.: PCT/GB98/01029

§ 371 Date: Jan. 10, 2000

§ 102(e) Date: Jan. 10, 2000

(87) PCT Pub. No.: WO98/46610

PCT Pub. Date: Oct. 22, 1998

(30) Foreign Application Priority Data

Apr. 11, 1997 (GB) ............................................. 9707413

(51) Int. Cl.[7] ...................... C07D 491/10; A61K 31/55
(52) U.S. Cl. ........................................ 540/543; 540/581
(58) Field of Search ................................. 540/543, 581

(56) References Cited

U.S. PATENT DOCUMENTS 5,428,159 A * 6/1995 Shieh et al. ................ 540/581
6,043,359 A * 3/2000 Crollner et al. ............. 540/581

FOREIGN PATENT DOCUMENTS

WO     WO-96/12692 A1 * 5/1996

OTHER PUBLICATIONS

Barton, D.H.R. et al, J. Chem. Soc., 1962, 806–817.*

Wen–Chung, Shied (1994) "Asymmetric Transformation of Either Enantiomer of Narwedine via Total Spontaneous Resolution Process, a Concise Solution to the Synthesis of (–)–Galanthamine" *Journal of Organic Chemistry* 59(18):5463–5465.

* cited by examiner

*Primary Examiner*—Richard L. Raymond
*Assistant Examiner*—Thomas C McKenzie
(74) *Attorney, Agent, or Firm*—Saliwanchik, Lloyd & Saliwanchik

(57) ABSTRACT

A process for the preparation of substantially single enantiomer (–)-narwedine comprises seeding a solution of racemic narwedine dissolved in a solvent with substantially single enantiomer (–)-narwedine, provided that if an added amine base is present the ratio solvent:added amine base is greater than 15:1.

15 Claims, No Drawings

PROCESS FOR PREPARING SINGLE ENANTIOMER NARWEDINE

FIELD OF THE INVENTION

This invention relates to a process for the preparation of substantially single enantiomer narwedine, or derivatives thereof, by a dynamic entrainment whereby racemic narwedine is seeded with its single enantiomer under dynamic conditions which do not require the presence of an added amine base, enabling production of single enantiomer of high purity and improved configurational stability.

BACKGROUND TO THE INVENTION (−)-Galanthamine is an alkaloid obtained from daffodils, and is under evaluation as a drug for the treatment of Alzheimer's disease. Synthetic methods for the preparation of galanthamine are therefore valuable, especially methods which lead to the desired single enantiomer, (−)-galanthamine. The production of high purity pharmaceutical grade (−)-galanthamine can be achieved by reduction of (−)-narwedine, and hence the purity of the (−)-narwedine or related precursor is also of importance.

In the first reported chemical synthesis of (−)-galanthamine [Barton and Kirby, J. Chem. Soc., 806, 1962] the key synthetic intermediate was racemic narwedine, although this was obtained in only very low yield (1.4%). Subsequently racemic narwedine was converted to (−)-narwedine by a method which was essentially a dynamic crystallisation process. Here crystallisation of (−)-narwedine was induced by addition of (+)-galanthamine, whilst a dynamic in situ racemisation enabled all the racemic material to be converted over to a single enantiomer. This essential in situ racemisation was found by Barton to be base-catalysed, and Barton employed the amine triethylamine as added base so as to facilitate this racemisation.

More recently, in an extension of Barton's work, a method has been developed in which racemic narwedine is resolved by seeding a supersaturated solution thereof in a solvent/amine base mixture with (−)-narwedine. The amine base is selected from pyridine or a trialkylamine, and the ratio solvent:base is from 1:9 to 15:1, most preferably about 9:1 [see Shieh and Carlson, J. Org. Chem., 59, 5463, 1994; WO 95/27715]. Again, the amine base is used to facilitate the vital in situ racemisation process.

Although an amine base such as triethylamine is useful in promoting in situ racemisation in the resolution process, this very property raises a number of problems which become prominent in large scale work. The most detrimental effect is that residual base becomes incorporated into the crystalline product, and the single enantiomer material prepared in this way does not remain enantiomerically-pure in the solid state, but undergoes slow racemisation upon storage. An added detrimental consequence of this is that material obtained in this way eventually becomes unsuitable for seeding of subsequent resolutions. Furthermore, the filtration time for collection of the resolved (−)-narwedine may become significant, and prolonged exposure of resolved (−)-narwedine to base-containing mother liquors renders it prone to racemisation, resulting in material of lower enantiomeric purity.

SUMMARY OF THE INVENTION

Despite the aforementioned requirement for an added amine base in the dynamic resolution of narwedine, we have surprisingly discovered that the dynamic entrainment can be performed on a preparative scale without the need for an added amine base.

According to the present invention, a process for the preparation of substantially single enantiomer (−)-narwedine comprises seeding a solution of racemic narwedine dissolved in a solvent with substantially single enantiomer (−)-narwedine, provided that if an added amine base is present the ratio solvent:amine base is greater than 15:1.

The present invention has a distinct and important advantage over the previously reported entrainment methods since the single enantiomer narwedine thus obtained is configurationally stable to racemisation in the solid state, due to the presence of substantially no added amine base. This, consequently, has advantages for large scale resolution work. The narwedine obtained is also of very high chemical purity, being free from exogenous organic amines, and moreover is in substantially single enantiomer form.

DESCRIPTION OF THE INVENTION

In the context of this Application, by substantially single enantiomer typically we mean an enantiomeric excess of at least 80% or higher, preferably at least 90%, more preferably higher. In fact, the process of the invention is capable of consistently achieving enantiomeric excesses of higher than 98%, and even higher than 99%.

By added amine base we mean amine base other than, or additional to, narwedine, such as pyridine or a trialkylamine, as used in prior art processes.

The dynamic entrainment process of the present invention comprises seeding a solution of racemic narwedine with (−)-narwedine. The dynamic entrainment may be carried out in an aqueous or alcoholic solvent, for example water, methanol, ethanol, isopropanol, n-propanol, especially ethanol, or any mixture of these solvents, preferably alcohol/water mixtures and more preferably an ethanol/water or methanol/water mixture.

Addition of a small amount of an amine base other than narwedine can be tolerated, provided that no detrimental effect is observed in the final product. For instance, the ratio of solvent: added amine base should be greater than 15:1, and preferably at least 20:1, by volume. Preferably, however, the process is carried out substantially, if not totally, in the absence of added amine base, for instance with the solvent: added amine base ratio being at least 30:1, preferably at least 40:1, and typically higher, eg. at least 50:1.

Once the racemic narwedine has been dissolved in an appropriate solvent, the narwedine solution is typically maintained at a temperature of between 40° C. and the reflux temperature of the mixture, preferably from around 60 to 100° C. The solution is then seeded with single enantiomer (−)-narwedine, typically from 1% to 30% by weight with respect to racemic narwedine, preferably from 5% to 15% by weight, and more preferably approximately 10% by weight, and then the solution allowed to cool to approximately 40° C., after which crystals of substantially single enantiomer (−)-narwedine are collected by filtration.

The present invention is further illustrated by way of the following Example.

EXAMPLE

A solution of racemic narwedine was prepared by dissolving racemic narwedine (4 g, 14 mmol) in ethanol (80 ml) and the solution heated at 85° C. for 1 hour to ensure complete dissolution of the racemic narwedine. Single enantiomer (−)-narwedine seed crystals (0.5 g, 1.4 mmol) were then added and the stirred mixture allowed to slowly cool to 40° C., with stirring continued at this temperature for 12 hours. The mixture was then allowed to reach 20° C. and the crystalline product collected by filtration to afford 3.72 g (93% yield) of (−)-narwedine in 99.1% ee.

What is claimed is:

1. A process for the preparation of substantially single enantiomer (−)-narwedine comprising seeding a solution of racemic narwedine dissolved in a solvent with 1 to 30% by weight substantially single enantiomer (−)-narwedine, based upon the amount of racemic narwedine, in the absence of added amine bases, wherein substantially single enantiomer (−)-narwedine comprises (−)-narwedine in an enantiomeric excess of at least 80%.

2. The process according to claim 1, wherein A seeding is carried out at 40° C. to 100° C., and crystallisation proceeds at around 40° C. or lower.

3. The process according to claim 1, wherein the solvent is selected from the group consisting of water, alcoholic solvents and mixtures thereof.

4. The process according to claim 3, wherein the alcoholic solvent is selected from the group consisting of methanol, ethanol, isopropanol, n-propanol, and mixtures thereof.

5. A process for the preparation of substantially single enantiomer (−)-galanthamine, comprising preparing substantially single enantiomer (−)-narwedine, and reducing that to give (−)-galanthamine, wherein said substantially single enantiomer (−)-galanthamine comprises (−)-galanthamine in an enantiomeric excess of at least 80%, and wherein said substantially single enantiomer (−)-narwedine is produced by a process comprising seeding a solution of racemic narwedine dissolved in a solvent with substantially single enantiomer (−)-narwedine in the absence of added amine base, wherein substantially single enantiomer (−)-narwedine comprises (−)-narwedine in an enantiomeric excess of at least 80%.

6. The process according to claim 2, wherein the solvent is selected from the group consisting of water, alcoholic solvents and mixtures thereof.

7. The process according to claim 6, wherein the alcoholic solvent is selected from the group consisting of methanol, ethanol, isopropanol, n-propanol, and mixtures thereof.

8. The process according to claim 5, wherein seeding is carried out at 40° C. to 100° C., and crystallisation proceeds at around 40° C. or lower.

9. The process according to claim 5, wherein the solvent is selected from the group consisting of water, alcoholic solvents and mixtures thereof.

10. The process according to claim 9, wherein the alcoholic solvent is selected from the group consisting of methanol, ethanol, isopropanol, n-propanol, and mixtures thereof.

11. The process according to claim 8, wherein the solvent is selected from the group consisting of water, alcoholic solvents and mixtures thereof.

12. The process according to claim 11, wherein the alcoholic solvent is selected from the group consisting of methanol, ethanol, isopropanol, n-propanol, and mixtures thereof.

13. The process according to claim 1, wherein said solution of racemic narwedine is seeded with 1 to 15% by weight substantially single enantiomer (−)-narwedine.

14. The process according to claim 1, wherein said solution of racemic narwedine is seeded with 5 to 15% by weight substantially single enantiomer (−)-narwedine.

15. The process according to claim 1, wherein said solution of racemic narwedine is seeded with 1 to 5% by weight substantially single enantiomer (−)-narwedine.

* * * * *

UNITED STATES PATENT AND TRADEMARK OFFICE
CERTIFICATE OF CORRECTION

PATENT NO. : 6,392,038 B1
DATED : May 21, 2002
INVENTOR(S) : Gerald Andrew Potter and Peter David Tiffin It is certified that error appears in the above-identified patent and that said Letters Patent is hereby corrected as shown below:

<u>Column 3,</u>
Line 13, "added amine bases" should read -- added amine base --.
Line 16, "wherein A seeding" should read -- wherein seeding --.

Signed and Sealed this

Sixteenth Day of July, 2002

*Attest:*

JAMES E. ROGAN
*Attesting Officer*   *Director of the United States Patent and Trademark Office*